United States Patent
Coburn et al.

(10) Patent No.: US 9,617,278 B2
(45) Date of Patent: Apr. 11, 2017

(54) ANTIMICROBIAL COMPOUNDS

(71) Applicants: Dow Global Technologies LLC, Midland, MI (US); Rohm and Haas Company, Philadelphia, PA (US)

(72) Inventors: Charles E. Coburn, Vernon Hills, IL (US); Thomas Koehler, Kreuzlingen (CH); Heather R. Mcginley, Highland Park, IL (US); Asghar A. Peera, Cary, IL (US)

(73) Assignees: ROHM AND HAAS COMPANY, Philadelphia, PA (US); DOW GLOBAL TECHNOLOGIES LLC, Midland, MI (US)

( * ) Notice: Subject to any disclaimer, the term of this patent is extended or adjusted under 35 U.S.C. 154(b) by 57 days.

(21) Appl. No.: 14/565,867

(22) PCT Filed: Jun. 12, 2013

(86) PCT No.: PCT/US2013/045418
§ 371 (c)(1),
(2) Date: Dec. 10, 2014

(87) PCT Pub. No.: WO2013/191988
PCT Pub. Date: Dec. 27, 2013

(65) Prior Publication Data
US 2015/0336983 A1    Nov. 26, 2015

Related U.S. Application Data
(60) Provisional application No. 61/661,518, filed on Jun. 19, 2012.

(51) Int. Cl.
| A01N 43/90 | (2006.01) |
| C07D 471/04 | (2006.01) |
| C07D 498/04 | (2006.01) |

(52) U.S. Cl.
CPC ........... *C07D 498/04* (2013.01); *A01N 43/90* (2013.01); *C07D 471/04* (2013.01)

(58) Field of Classification Search
None
See application file for complete search history.

(56) References Cited

U.S. PATENT DOCUMENTS

| 5,480,643 A | 1/1996 | Donovan et al. |
| 6,034,138 A | 3/2000 | Synodis et al. |
| 7,319,131 B2 | 1/2008 | Swedo et al. |
| 8,741,928 B2 | 6/2014 | Coburn et al. |
| 2013/0267604 A1 | 10/2013 | Coburn et al. |

FOREIGN PATENT DOCUMENTS

| WO | 2004071412 A2 | 8/2004 |
| WO | 2008003606 A1 | 1/2008 |
| WO | 2010039923 A2 | 4/2010 |

OTHER PUBLICATIONS

Langdale-Smith, "Facile synthesis of new heterocycles from glutaraldehyde", J. Organic Chem., vol. 36, No. 1, pp. 226-227 (1971).
Wong, et al., "Pyridine-Derived Oxazolidines as Chiral 3-Alkyl-4,5-dihydropyridinium and 3-Alkyl-3,4,5,6-tetrahydropyridinium Salt Equivalents", J. Organic Chem., vol. 62, No. 3, pp. 729-733 (1997).

*Primary Examiner* — Leslie A. Royds Draper
(74) *Attorney, Agent, or Firm* — Tifani M. Edwards

(57) ABSTRACT

Provided are compounds which are useful for controlling microorganisms in aqueous or water-containing systems or in systems which are exposed to moisture, including at elevated temperature. The antimicrobial compounds are of the formula I:

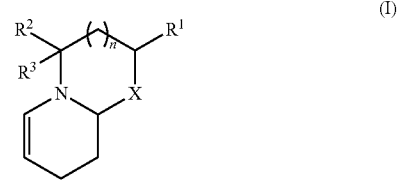

wherein n, $R^1$, $R^2$, $R^3$, and X are as defined herein.

6 Claims, No Drawings

ANTIMICROBIAL COMPOUNDS

FIELD

The invention relates generally to antimicrobial compounds and methods of their use for the control of microorganisms in aqueous or water-containing systems or in systems which are exposed to moisture.

BACKGROUND

Protecting aqueous systems from microbial contamination is critical to the success of many industrial processes, including oil or natural gas production operations. In oil and gas operations, microorganism contamination from both aerobic and anaerobic bacteria can cause serious problems such as reservoir souring (mainly caused by anaerobic sulfate-reducing bacteria (SRB)), microbiologically influenced corrosion (MIC) on metal surfaces of equipment and pipelines, and degradation of polymer additives.

Glutaraldehyde is a known antimicrobial compound that is used to control the growth of microorganisms in aqueous systems and fluids, including those found in oil and gas operations. Glutaraldehyde, however, is susceptible to a number of drawbacks. For instance, it can degrade over time at the elevated temperatures often encountered in the oil and gas production environment. The material can also be inactivated by other common oilfield chemicals such as bisulfate salts and amines These conditions can leave oilfield infrastructure (wells, pipelines, etc.) and formations susceptible to microbial fouling.

The problem addressed by this invention is the provision of antimicrobial systems with improved thermal and chemical stability.

STATEMENT OF INVENTION

We have now found that compounds of formula I as described herein are capable of controlling microorganisms in aqueous or water-containing systems or in systems which are exposed to moisture, including those found in oil and gas operations. Advantageously, unlike the free aldehyde, the compounds of formula I are more stable at elevated temperatures, thus permitting extended control of microbial fouling. In addition, the compounds may exhibit improved stability in the presence of other chemical species that would otherwise degrade the free glutaraldehyde, such as reducing or oxidizing agents including bisulfites, and amines In one aspect, therefore, the invention provides compounds of formula I:

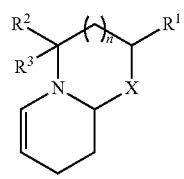

(I)

wherein n is 0 or 1; $R^1$, $R^2$, and $R^3$ are independently H, linear or branched $C_1$-$C_{10}$ alkyl, or $C_3$-$C_8$ cycloalkyl, or $R^2$ and $R^3$ together with the carbon to which they are attached form $C_3$-$C_8$ cycloalkyl; and X is O or $NR^4$, wherein $R^4$ is H or $C_1$-$C_6$ alkyl.

In another aspect, the invention provides methods for controlling microorganisms in aqueous or water-containing systems or in systems which are exposed to moisture. In some embodiments, the system has a temperature of at least 40° C. The method comprises contacting the system with a compound of formula I as described herein.

DETAILED DESCRIPTION

"Alkyl," as used in this specification encompasses straight and branched chain aliphatic groups having the indicated number of carbon atoms. Exemplary alkyl groups include, without limitation, methyl, ethyl, propyl, isopropyl, butyl, isobutyl, sec-butyl, tert-butyl, pentyl, hexyl, heptyl, and octyl.

The term "cycloalkyl" refers to saturated and partially unsaturated cyclic hydrocarbon groups having the indicated number of ring carbon atoms. Preferred cycloalkyl groups include, without limitation, cyclopentyl, cyclohexyl, cycloheptyl, and cyclooctyl. The cycloalkyl is optionally substituted with linear or branched $C_1$-$C_6$ alkyl.

For the purposes of this specification, the meaning of "microorganism" includes, but is not limited to, bacteria, fungi, algae, archaea, and viruses. The words "control" and "controlling" should be broadly construed to include within their meaning, and without being limited thereto, inhibiting the growth or propagation of microorganisms, killing microorganisms, disinfection, and/or preservation against microorganism re-growth. In some embodiments, the microorganisms are bacteria. In some embodiments, the microorganisms are aerobic bacteria. In some embodiments, the microorganisms are anaerobic bacteria. In some embodiments, the microorganisms are sulfate reducing bacteria (SRB). In some embodiments, the microorganisms are acid producing bacteria (APB). In some embodiments, the microorganisms are archaea.

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

As noted above, the invention provides compounds and methods of using them for the control of microorganisms in aqueous or water-containing systems or in systems which are exposed to moisture, including those found in oil and gas operations.

Compounds of the invention may be represented by the formula I:

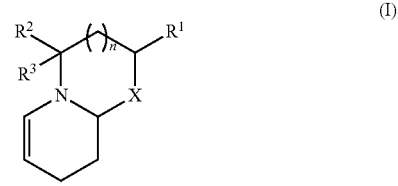

(I)

wherein n is 0 or 1; $R^1$, $R^2$, and $R^3$ are independently H, linear or branched $C_1$-$C_{10}$ alkyl, or $C_3$-$C_8$ cycloalkyl, or $R^2$ and $R^3$ together with the carbon to which they are attached form $C_3$-$C_8$ cycloalkyl; and X is O or $NR^4$, wherein $R^4$ is H or $C_1$-$C_6$ alkyl.

In some embodiments, $R^1$ in the compounds of formula I is H.

In some embodiments, $R^2$ is H and $R^3$ is linear or branched $C_1$-$C_{10}$ alkyl.

In some embodiments, $R^2$ is H and $R^3$ is $C_3$-$C_8$ cycloalkyl.

In some embodiments, $R^2$ and $R^3$ are independently linear or branched $C_1$-$C_{10}$ alkyl.

In some embodiments, n is 0.

In some embodiments, X is O.

In some embodiments, X is $NR^4$, wherein $R^4$ is H or $C_1$-$C_6$ alkyl. In some embodiments, $R^4$ is H.

Exemplary compounds of formula I include the following:

| Name | Structure |
|------|-----------|
| 2-butyl-3-ethyl-3,7,8,8a-tetrahydro-2H-oxazolo[3,2-a]pyridine | 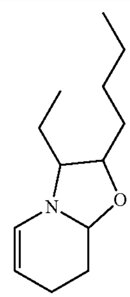 |
| 2-(heptan-3-yl)-3-methyl-3,7,8,8a-tetrahydro-2H-oxazolo[3,2-a]pyridine | 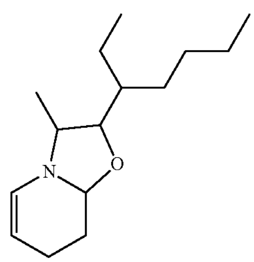 [SMILES: CCCCC(CC)C1OC2CCC=CN2C1C] |
| 2,3-dimethyl-3,7,8,8a-tetrahydro-2H-oxazolo[3,2-a]pyridine | 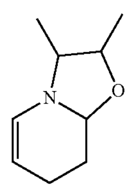 |
| 3,3-dimethyl-3,7,8,8a-tetrahydro-2H-oxazolo[3,2-a]pyridine | 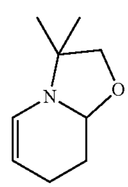 |
| 2',7',8',8a'-tetrahydrospiro[cyclohexane-1,3'-oxazolo[3,2-a]pyridine] | 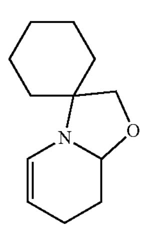 [SMILES: C1=CN2C(CC1)OCC21CCCCC1] |
| 2,3,4,8,9,9a-hexahydropyrido[2,1-b][1,3]oxazine | 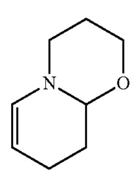 |
| 2-ethyl-2,3,4,8,9,9a-hexahydro-1H-pyrido[1,2-a]pyrimidine | |

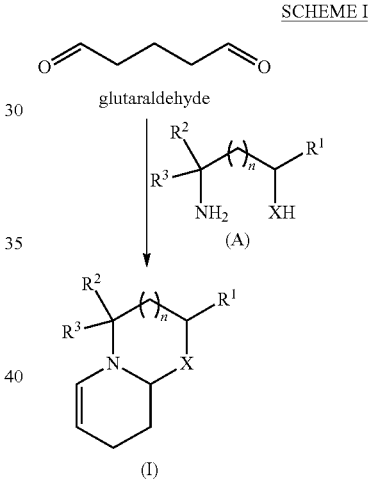

In some embodiments, 2,3,4,8,9,9a-hexahydropyrido[2,1-b][1,3]oxazine is excluded as a compound of the invention.

Compounds of formula I may be prepared, for example, as depicted in Scheme I. Typically, the glutaraldehyde is mixed with amine compound A in a suitable solvent, such as water. The mixture may be stirred for sufficient time to allow the reaction to occur and the desired compound of formula I to form. The product may be used as is, or optionally further purified using techniques well known to those skilled in the art, such as crystallization, chromatography, distillation, extraction, etc.

SCHEME I

The compound A used in the synthesis described above is generally an amine compound that contains an additional amine or hydroxyl group. Examples include: 3-aminooctan-4-ol, 2-amino-4-ethyloctan-3-ol, (1-aminocyclohexyl)methanol, 2-amino-2-methylpropan-1-ol, 3-aminobutan-2-ol, 3-amino-1-propanol, pentane-1,3-diamine, or 2-amino-4-isopropylheptan-3-ol. Such compounds may be commercially available and/or may be readily prepared by those skilled in the art.

As noted above, it is not necessary in the invention that the compounds of formula I be isolated or purified from the reaction mixture in which they were synthesized, and in some embodiments it may be preferred that the reaction mixture be used without purification for the control of microorganisms. Such mixture may contain isomers of the compound, or polymeric species or other byproducts that are inert or that may also provide microbial control.

The compounds of formula I may release glutaraldehyde when heat-activated. Unlike the free aldehyde, however, the compounds are more stable at elevated temperatures thus permitting extended control of microbial fouling. In addition, the compounds may exhibit improved stability in the presence of other chemical species that would otherwise degrade the free aldehydes, such as bisulfites, and amines.

Because of their stability and heat activation characteristics, the compounds of the invention are useful for controlling microorganisms for extended periods of time in aqueous or water-containing systems or in systems which are exposed to moisture, including those that are at elevated temperatures. The compounds of the invention are also useful for incorporation into products which are manufactured or stored at elevated temperatures. The compounds are also useful for controlling microorganisms aqueous or water-containing systems that may be present or used in oil or natural gas applications, paper machine white water, industrial recirculating water, starch solutions, latex or polymer emulsions, coatings or building products or household products or personal care products which are manufactured at elevated temperatures, plastics, hot rolling machining fluids, or industrial dishwashing or laundry fluids, animal biosecurity fluids, or high level disinfection fluids. In some embodiments, the aqueous or water-containing system may be present or used in oil or natural gas applications. Examples of such systems include, but are not limited to, fracturing fluids, drilling fluids, water flood systems, oil field water, and produced fluids.

In some embodiments, the system may be at a temperature of 40° C. or greater, alternatively 55° C. or greater, alternatively 60° C. or greater, alternatively 70° C. or greater, or alternatively 80° C. or greater.

In addition to their heat stability, the compounds may further be effective when a deactivating agent, such as a source of bisulfite ion or amines is present in the system.

A person of ordinary skill in the art can readily determine, without undue experimentation, the effective amount of the compound that should be used in any particular application to provide microbial control. By way of illustration, a suitable concentration, based on the equivalent of glutaraldehyde that is potentially released (assuming 100% release) by the formula I compound is typically at least about 1 ppm, alternatively at least about 5 ppm, alternatively at least about 50 ppm, or alternatively at least about 100 ppm by weight. In some embodiments, the concentration is 2500 ppm or less, alternatively 1500 ppm or less, or alternatively 1000 ppm or less. In some embodiments, the aldehyde equivalent concentration is about 100 ppm.

The compounds of formula I may be used in the system with other additives such as, but not limited to, surfactants, ionic/nonionic polymers and scale and corrosion inhibitors, oxygen scavengers, nitrate or nitrite salts, and/or additional antimicrobial compounds.

Some embodiments of the invention will now be described in detail in the following Examples.

EXAMPLES

Example 1

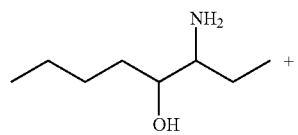

-continued

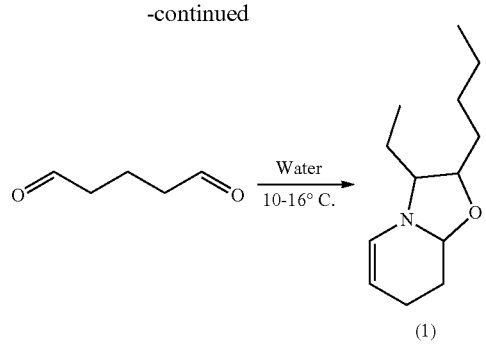

(1)

A three neck 250 mL round bottom flask equipped with a stir bar, thermocouple, addition funnel capped with nitrogen inlet and condenser is charged with 3-aminooctan-4-ol (85%, 42.7 g, 0.25 mols, 1.0 equivalents). The flask is cooled down to approximately 10° C. under ice/water bath. Once the temperature is reached, glutaraldehyde (50%, 50.0 g, 0.25 mols, 1.0 equivalents) is added drop wise over a period of 45 minutes. The reaction temperature is maintained by cooling the bath and by controlled addition of glutaraldehyde. After complete addition of glutaraldehyde, the transparent reaction mixture turns milky/opaque and a viscous sticky solid starts forming making stirring difficult. After 2 h, 100 mL of ethyl acetate is added to the reaction mixture and vigorously stirred under nitrogen. The entire content of the flask dissolves in ethyl acetate. The ethyl acetate layer is washed twice with 100 mL of water and the organic layer dried in magnesium sulfate. After filtering the MgSO$_4$, the organic solvent is stripped off under rotary evaporator and this results in approximately 43 g of crude material (82.3% yield). GC-MS analysis confirms the presence of four isomers of (1), 2-butyl-3-ethyl-3,7,8,8a-tetrahydro-2H-oxazolo[3,2-a]pyridine and CI-MS shows [M+H]=210.

Example 2

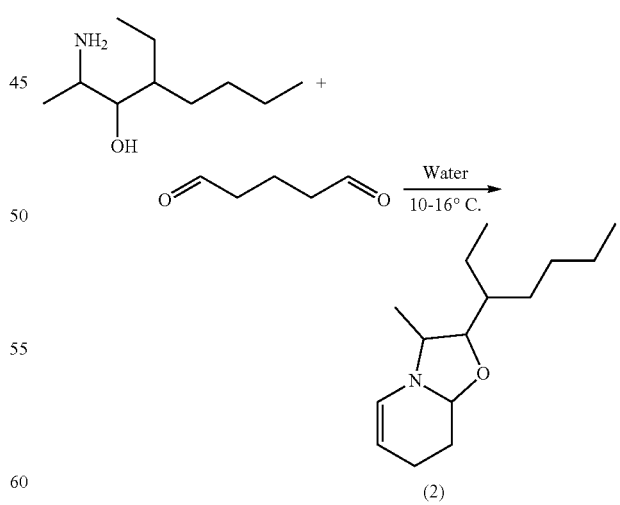

(2)

A three neck 50 mL round bottom flask equipped with a stir bar, thermocouple, addition funnel capped with nitrogen inlet and condenser is charged with 2-amino-4-ethyloctan-3-ol (100%, 8.7 g, 0.05 mols, 1.0 equivalents) and 10 mL of water. The flask is cooled down to approximately 10° C.

under ice/water bath. Once the temperature is reached, glutaraldehyde (50%, 10.0 g, 0.05 mols, 1.0 equivalents) is added drop wise over a period of 15 minutes. The reaction temperature is maintained by cooling the bath and by controlled addition of glutaraldehyde. After complete addition of glutaraldehyde, the transparent reaction mixture turns milky/opaque and a viscous sticky solid starts forming making stirring difficult. After 1 h, 50 mL of ethyl acetate is added to the reaction mixture and vigorously stirred under nitrogen. The entire contents of the flask dissolve in ethyl acetate. The ethyl acetate layer is washed twice with 50 mL of water and the organic layer dried in magnesium sulfate. After filtering the $MgSO_4$, the organic solvent is stripped off under rotary evaporator and this results in approximately 10.93 g of crude material (91.8% yield). GC-MS analysis confirms the presence of six isomers of (2), 2-(heptan-3-yl)-3-methyl-3,7,8,8a-tetrahydro-2H-oxazolo[3,2-a]pyridine and CI-MS shows [M+H]=238.

Example 3

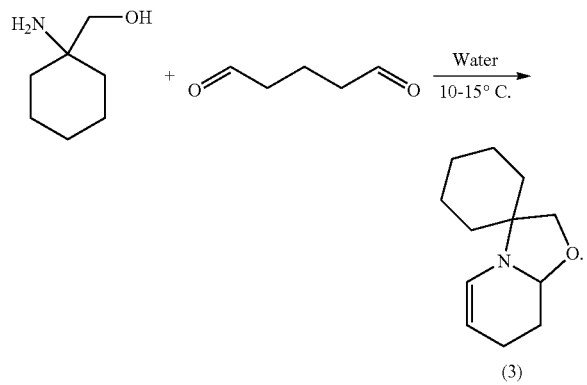

(3)

A three neck 50 mL round bottom flask equipped with a stir bar, thermocouple, addition funnel capped with nitrogen inlet and condenser is charged with (1-aminocyclohexyl) methanol (100%, 3.23 g, 0.025 mols, 1.0 equivalents) and 6 mL of water. The flask is cooled down to approximately 10° C. under ice/water bath. Once the temperature is reached, glutaraldehyde (50%, 5.0 g, 0.025 mols, 1.0 equivalents) is added drop wise over a period of 10 minutes. The reaction temperature is maintained by cooling the bath and by controlled addition of glutaraldehyde. Upon complete addition of glutaraldehyde, the reaction mixture very quickly turns viscous and stirring is very difficult. To the reaction mixture is added 30 mL of ethyl acetate to dissolve the solid, however only small amounts of material dissolve in ethyl acetate in this reaction. The yellow ethyl acetate solution is decanted and excess solvent removed by rotary evaporator. This procedure results in 1.13 g (21.7% yield) of yellow viscous material. GC-MS analysis confirms the presence of (3), 2',7',8',8a'-tetrahydrospiro[cyclohexane-1,3'-oxazolo[3,2-a]pyridine] and CI-MS shows [M+H]=194.

Example 4

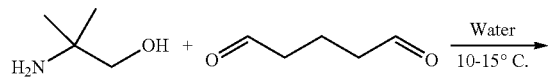

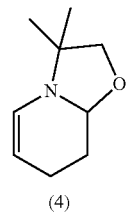

(4)

A three neck 50 mL round bottom flask equipped with a stir bar, thermocouple, addition funnel capped with nitrogen inlet and condenser is charged with 2-amino-2-methylpropan-1-ol (95%, 7.8 g, 0.083 mols, 1.0 equivalents). The flask is cooled down to approximately 10° C. under ice/water bath. Once the temperature is reached, glutaraldehyde (50%, 16.7 g, 0.083 mols, 1.0 equivalents) is added drop wise over a period of 15-20 minutes. The reaction temperature is maintained by cooling the bath and by controlled addition of glutaraldehyde. After complete addition of glutaraldehyde, the transparent reaction mixture turns milky/opaque and a viscous sticky solid starts forming making stirring difficult. The reaction is stopped and the GC of the material is taken and a peak at 11.99 minutes is observed which corresponds to compound (4). The GC has some minor impurities in the high retention region. 20 mL of ethyl acetate is added to the reaction mixture and vigorously stirred under nitrogen. The entire content of the flask dissolve in ethyl acetate. The ethyl acetate layer is washed twice with 25 mL of water and the organic layer dried in magnesium sulfate. After filtering the $MgSO_4$, the organic solvent is stripped off under a rotary evaporator and this results in approximately 6.72 g of crude material (52% yield). However, when the GC of the dried sample is taken again, the peak at 11.99 minutes becomes significantly smaller by area while the high retention impurities became dominant peaks indicating that compound (4) is of limited stability. GC-MS analysis confirms the presence of (4), 3,3-dimethyl-3,7,8,8a-tetrahydro-2H-oxazolo[3,2-a]pyridine and CI-MS shows [M+H]=154, however this is not the major compound in the crude mixture.

Example 5

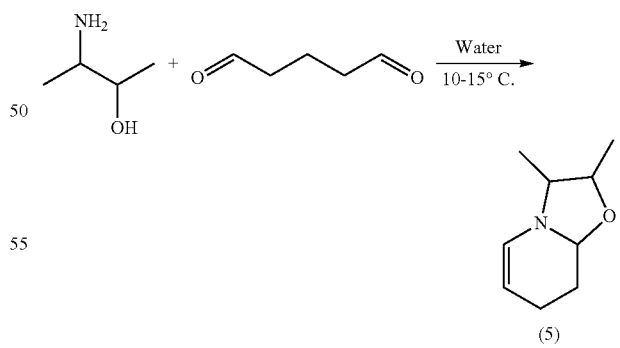

(5)

A three neck 100 mL round bottom flask equipped with a stir bar, thermocouple, addition funnel capped with nitrogen inlet and condenser is charged with 3-aminobutan-2-ol (100%, 8.9 g, 0.1mols, 1.0 equivalent). The flask is cooled to approximately 10° C. under ice/water bath. Once the temperature is reached, glutaraldehyde (50%, 20.0 g, 0.1 mols, 1.0 equivalents) is added drop wise over a period of 20 minutes. The reaction temperature is maintained by cooling the bath and by controlled addition of glutaraldehyde. After complete addition of glutaraldehyde, the transparent reaction mixture turns opaque and a viscous sticky solid starts forming making stirring difficult. The reaction is stopped and the GC of the material is taken and four isomeric peaks between 11.92 and 12.30 minutes are observed which corresponded to compound (5). The GC has some minor impurities in the high retention region. 20 mL of ethyl acetate is added to the reaction mixture and vigorously stirred under nitrogen. The entire content of the flask dissolves in ethyl acetate. The ethyl acetate layer is washed twice with 25 mL of water and the organic layer dried in magnesium sulfate. After filtering the MgSO$_4$, the organic solvent is stripped off under a rotary evaporator and this results in approximately 7.1 g of crude material (46.4% yield). However, when the GC of the dried sample is taken again, the peak at 11.92 and 12.30 minutes becomes significantly smaller by area while the high retention impurities become dominant peaks indicating that compound (5) has limited stability. GC-MS analysis confirms the presence of (5), 2,3-dimethyl-3,7,8,8a-tetrahydro-2H-oxazolo[3,2-a]pyridine and CI-MS showed [M+H]=154, however this was not the major compound in the crude mixture.

Example 6

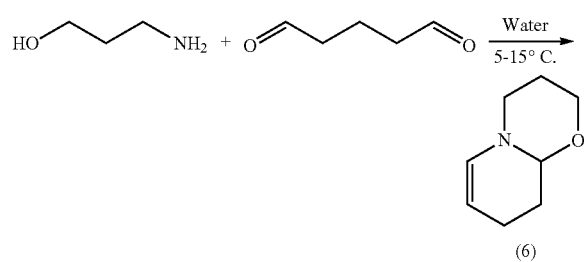

A three neck 100 mL round bottom flask equipped with a stir bar, thermocouple, addition funnel capped with nitrogen inlet and condenser is charged with 3-amino-1-propanol (100%, 7.52 g, 0.1 mols, 1.0 equivalent). The flask is cooled to approximately 10° C. under ice/water bath. Once the temperature is reached, glutaraldehyde (50%, 20.0 g, 0.1 mols, 1.0 equivalents) is added drop wise over a period of 20 minutes. The reaction temperature is maintained by cooling the bath and by controlled addition of glutaraldehyde. After complete addition of glutaraldehyde, the transparent reaction mixture turns viscous and yellow in color. There is no sign of any solid crashing out of solution. The reaction is allowed to stir under ice/water bath for 30 minutes and gradually warmed to room temperature. As the temperature of the reaction mixture increases, the yellow material turns brown. GC of the reaction mixture shows that all the starting material is consumed and a prominent peak is seen at retention time of 12.15 minutes. The reaction mixture is dissolved in 25 mL of ethyl acetate and vigorously stirred under nitrogen. The entire contents of the flask dissolves in ethyl acetate. The ethyl acetate layer is washed thrice with 25 mL of water and the organic layer dried in magnesium sulfate. After filtering the MgSO$_4$, the organic solvent is stripped off under a rotary evaporator and this results in approximately 3.83 g of crude material (58% yield). GC-MS analysis confirms the presence of (6), 2,3,4,8,9,9a-hexahydropyrido[2,1-b][1,3]oxazine and CI-MS showed [M+H]=139.9.

Example 7

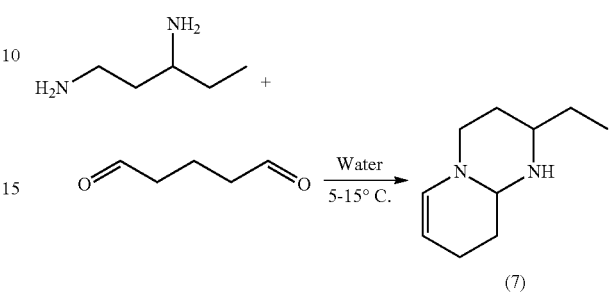

A three neck 100 mL round bottom flask equipped with a stir bar, thermocouple, addition funnel capped with nitrogen inlet and condenser is charged with pentane-1,3-diamine (100%, 10.2 g, 0.1 mols, 1.0 equivalent). The flask is cooled to approximately 10° C. under ice/water bath. Once the temperature is reached, glutaraldehyde (50%, 20.0 g, 0.1 mols, 1.0 equivalents) is added drop wise over a period of 20 minutes. The reaction temperature is maintained by cooling the bath and by controlling addition of glutaraldehyde. After complete addition of glutaraldehyde, the transparent reaction mixture turns viscous and yellow in color. At this point 15 mL of water is added to assist with the stirring. There is no sign of any solid crashing out of solution. The reaction is allowed to stir under ice/water bath for 30 minutes and gradually warmed to room temperature. GC of the reaction mixture shows that all the starting material is consumed and peaks are seen at retention time of 13.51 and 13.89 minutes. The peaks corresponds to the different isomers of compound (7). The reaction mixture is dissolved in 25 mL of ethyl acetate and vigorously stirred under nitrogen. The entire contents of the flask dissolve in ethyl acetate. The ethyl acetate layer is washed thrice with 25 mL of water and the organic layer dried in magnesium sulfate. After filtering the MgSO$_4$, the organic solvent is stripped off under a rotary evaporator and this results in approximately 7.60 g of crude material (45.8% yield). GC-MS analysis confirms the presence of (7), 2-ethyl-2,3,4,8,9,9a-hexahydro-1H-pyrido[1,2-a]pyrimidine and CI-MS showed [M+H]=167.

Example 8

Assay for Biocidal Efficacy at Room Temperature
Glutaraldehyde and Compounds 1 and 2 are tested for biocidal activity against a pool of aerobic organisms at room temperature and against sulfate reducing bacteria (SRB) at room temperature. Tests are performed as follows:
a. Stock preparation. Glutaraldehyde (50% in water) and Compounds 1 and 2 are each dissolved in DMSO to a concentration of 200 mM, which is equivalent to 20,000 ppm of free glutaraldehyde.
b. Aerobic Bacteria—a mixed pool of 6 bacterial species at ~5×10$^6$ CFU/mL in phosphate buffered saline is distributed into a 96-well plate. Each well receives an independent chemical treatment of glutaraldehyde or Compound 1 or 2 at concentrations ranging from 200 ppm to 12 ppm glutaraldehyde. A control treatment of DMSO alone is also included. Each condition is tested in triplicate. After set periods of incubation (1, 4, and 24 h), the number of surviving cells in each well are enumerated by dilution to extinction in a medium containing resazurin dye as an indicator.

c. Sulfate Reducing Bacteria (SRB)—SRB testing is performed as for the aerobic bacteria with the following modifications: the species *Desulfovibrio longus* is tested in anaerobic PBS and the enumeration of surviving cells is performed in a medium containing soluble iron as an indicator.

d. Results: Values indicate the minimum dose needed (in ppm) to achieve 3-log reduction in bacteria levels. "n/a" indicates the threshold was not met at any of the tested doses. "N.D" indicates data not available.

| bacteria type | 1 hour | | | 4 hours | | | 24 hours | | |
|---|---|---|---|---|---|---|---|---|---|
| | glut | 1 | 2 | glut | 1 | 2 | glut | 1 | 2 |
| aerobic | 26 | n/a | n/a | 26 | n/a | n/a | 26 | n/a | n/a |
| SRB | 89 | n/a | 200 | 18 | 200 | >200 | <12 | 26 | N.D. |

Compounds 1 and 2 do not show significant biocidal activity against aerobic bacteria at room temperature. They do show some activity against SRB, but are not as effective as glutaraldehyde.

Assay for Biocidal Efficacy at Elevated Temperature

Compound 1 (208 mg) is dissolved in DMSO (5 mL) to yield a 200 mM solution such that the glutaraldehyde-equivalent concentration of the stock solution is 20,000 ppm. The bacterial strain *Thermus thermophilus* (ATCC 27634) is maintained at 70° C. After 24-48 hours of growth, 10 mL of bacterial culture are harvested by spinning in a Beckman-Coulter benchtop centrifuge at 3000 rpm for 15 min. The cell pellet is resuspended in 100 mL of phosphate-buffered saline (PBS) to give approximately $5 \times 10^5$ CFU/mL and aliquoted into 10 mL portions in glass test tubes fitted with screw caps. Samples are equilibrated to 37, 55, or 70° C. for 30 min and then treated with glutaraldehyde or Compound 1 at 50 ppm glutaraldehyde equivalent. The treated samples are returned to their respective equilibration temperatures for 4 h and then enumerated for surviving bacteria. After 24 h, the process is repeated by adding fresh grown bacteria to the samples to re-challenge the biocide. The samples are again enumerated after 4 h.

Results are reported in terms of log kill of treated bacterial populations relative to an untreated control at each temperature. For values listed as ">x," actual kill may have been higher but could not be detected by this assay. Compound 1 shows equivalent activity to glutaraldehyde at each 70° C. but is less effective at the lower temperatures.

| | 4 hr | | 24 hr | |
|---|---|---|---|---|
| temperature | glut | 1 | glut | 1 |
| 37° C. | >3 | >3 | >4 | 2 |
| 55° C. | >3 | >3 | >3 | 1 |
| 70° C. | >4 | >4 | >4 | >4 |

We claim:

1. A compound of formula I:

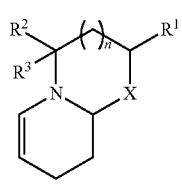

(I)

wherein n is 0 or 1; $R^1$, $R^2$, and $R^3$ are independently H, linear or branched $C_1$-$C_{10}$ alkyl, or $C_3$-$C_8$ cycloalkyl, or $R^2$ and $R^3$ together with the carbon to which they are attached form $C_3$-$C_8$ cycloalkyl; and X is O or $NR^4$, wherein $R^4$ is H or $C_1$-$C_6$ alkyl, provided that the compound is not 2,3,4,8,9,9a-hexahydropyrido[2,1-b][1,3]oxazine.

2. The compound of claim 1 wherein $R^1$ is H, and $R^2$ and $R^3$ are independently linear or branched $C_1$-$C_{10}$ alkyl.

3. The compound of claim 1 wherein $R^3$ is H, and $R^1$ and $R^2$ are independently linear or branched $C_1$-$C_{10}$ alkyl.

4. The compound of claim 1 wherein n is 0.

5. The compound of claim 1 wherein X is O.

6. The compound of claim 1 that is: 2-butyl-3-ethyl-3,7,8,8a-tetrahydro-2H -oxazolo[3,2-a]pyridine; 2',7',8',8a'-tetrahydrospiro[cyclohexane-1,3'-oxazolo[3,2-a]pyridine];2-(heptan-3-yl)-3-methyl-3,7,8,8a-tetrahydro-2H-oxazolo[3,2-a]pyridine; 2,3-dimethyl-3,7,8,8a-tetrahydro-2H-oxazolo[3,2-a]pyridine; 3,3-dimethyl-3,7,8,8a-tetrahydro-2H-oxazolo[3,2-a]pyridine; or 2-ethyl-2,3,4,8,9,9a-hexahydro-1H-pyrido[1,2-a]pyrimidine.

* * * * *